United States Patent [19]

Monte et al.

[11] 4,094,853

[45] June 13, 1978

[54] ALKOXY TITANATE SALTS USEFUL AS COUPLING AGENTS

[75] Inventors: Salvatore J. Monte, Staten Island, N.Y.; Gerald Sugerman, Allendale, N.J.

[73] Assignee: Kenrich Petrochemicals, Inc., Hudson, N.J.

[21] Appl. No.: 577,922

[22] Filed: May 15, 1975

[51] Int. Cl.² ................................................ C08K 9/04
[52] U.S. Cl. .............................. 260/40 R; 260/42.14; 260/429.5
[58] Field of Search ............... 260/42.14, 429.5, 40 R; 428/406, 403; 106/299, 308 S, 308 Q

[56] References Cited

U.S. PATENT DOCUMENTS

| | | | |
|---|---|---|---|
| 3,337,391 | 8/1967 | Clayton et al. | 260/429.5 X |
| 3,617,333 | 11/1971 | Brown | 428/406 |
| 3,697,474 | 10/1972 | Morris et al. | 260/42.14 X |

FOREIGN PATENT DOCUMENTS 733,224  7/1955  United Kingdom.

*Primary Examiner*—Sandra M. Person
*Attorney, Agent, or Firm*—Bert J. Lewen

[57] ABSTRACT

A composition of matter comprising the reaction product of a comminuted inorganic material and an organotitanate having the formula $(RO)Ti(OCOR')_3$ wherein R is a monovalent alkyl, alkenyl, alkynyl or aralkyl group having from 1 to 30 carbon atoms or a substituted derivative thereof, R' is a monovalent organic group the total number of carbon atoms in the three R' groups in a molecule being not more than 14; and polymeric materials containing such reaction products.

8 Claims, No Drawings

4,094,853

ALKOXY TITANATE SALTS USEFUL AS COUPLING AGENTS

BACKGROUND OF THE INVENTION

Inorganic materials have long been used as fillers, pigments, reinforcements and chemical reactants in polymers. In general, these inorganic materials are hydrophilic, that is, easily wetted by water or able to absorb water, but their compatibility with organic polymers is limited. Because of this limited compatibility, the full potential of color, reinforcement, or chemical reactivity of the inorganic materials is not realized.

To overcome these difficulties, wetting agents have been used to minimize interfacial tension: but wetting agents, too, have serious deficiencies. In particular, relatively large proportions are necessary to produce adequate wetting of the finely divided inorganics. When used in large proportions, the wetting agents markedly detract from the properties of the finished composite. Coupling agents have been developed to overcome this difficulty. These fall into two main classes. The first, the more widely used, are trialkoxy organo functional silanes. Their activity is based upon chemical interaction between the alkoxy portion of the silane and filler and the chemical reaction of the organo functional portion with the polymer matrix. This provides a direct chemical link between the polymer and filler. But silanes have drawbacks. They are typically highly flammable, difficult to handle, and not easily worked into many polymer systems. Where the polymers do not contain functional groups or where the filler does not contain acidic protons, the silanes are often ineffective because of their inability to interact. For example, silanes are ineffective in thermoplastic hydrocarbons and fillers, such as carbon black, and to a large degree, calcium carbonate and sulfur.

The second group of coupling agents includes the organo-titanates which may be prepared by reacting tetraalkyl titanates with aliphatic or aromatic carboxylic acids. Of particular interest are the di- or trialkoxy acyl titanates or certain alkoxy triacyl titanates. These titanates, however, have serious drawbacks: e.g., they tend to decompose at temperatures frequently used in preparing many polymers; they tend to discolor certain inorganic materials used with polymer systems; and they are not compatible with many polymer systems.

DETAILS OF THE INVENTION

The subject invention relates to compositions of matter which are the reaction products of comminuted inorganic materials and alkoxy titanium salts having the following formula: $(RO)Ti(OCOR')_3$.

wherein R is a monovalent alkyl, alkenyl, alkynyl or aralkyl group having from 1 to about 30 carbon atoms or a substituted derivative thereof. The R group may be saturated or unsaturated, linear or branched, and may have from 1 to 6 substitutions including halogen, amino, epoxy, cyano, ether, thioether, carbonyl, aromatic nitro, or acetal. In a particular molecule, all of the R groups may be the same or different, so long as they fall within the above class. It is preferred that the R group be alkyl having 1 to 6 carbon atoms and be all the same.

In the acyl ligand, (OCOR'), the R' may be hydrogen or a monovalent organic group having from 1 to about 12 carbon atoms; particularly, an alkyl, alkenyl, aryl, aralkyl or alkaryl group. The aryl groups may be substituted or unsubstituted phenyl or naphthyl groups, preferably containing up to 12 carbon atoms. Additionally, the R' group may be substituted with halo, amino, epoxy, ether, thioether, ester, cyano, carboxyl and/or aromatic nitro substituents. Generally up to about six substituents may occur per R' group. The R' group may contain intermediate hetero atoms such as sulfur or nitrogen in the main or pendant substituents.

The total number of carbon atoms in the three R' groups is not more than 14. Most desirably, all R's are the same. It is preferred that all R' groups be vinyl, methylvinyl or aminomethyl.

A wide variety of ligands, subject to the limitations heretofore expressed, may be used in the practice of this invention. The most suitable depends upon the filler-polymer system and to a lesser degree upon the curative and/or extender systems employed.

Examples of specific R ligands are: methyl, propyl, cyclopropyl, cyclohexyl, tetraethyloctadecyl, 2,4-dichlorobenzyl, 1-(3-bromo-4-nitro-7-acetylnaphthyl)ethyl, 2-cyano-furyl, 3-thiomethyl-2-ethoxy-1-propyl and methallyl.

Examples of the R' groups are numerous. These include straight chain, branched chain and cyclic alkyl groups such as hexyl, heptyl, octyl, decyl and dodecyl. Alkenyl groups including hexenyl, octenyl and dodecenyl.

Halo-substituted groups include bromohexyl. One or more halogen atoms may be present, as for example in difluorohexyl or tetrabromooctyl. Ester-substituted aryl and alkyl groups include 4-carboxyethylcapryl and 3-carboxymethyltoluyl. Amino-substituted groups include aminocaproyl, aminostearyl, aminohexyl, aminolauryl and diaminooctyl.

In addition to the foregoing aliphatic groups, groups containing hetero-atoms, such as oxygen, sulfur or nitrogen, in the chain may also be used. Examples of these radicals are ethers of the alkoxyalkyl type, including methoxyhexyl and ethoxydecyl. Alkylthioalkyl groups include methylthiododecyl groups. Primary, secondary and tertiary amines may also serve as the terminal portion of the hydrophobic group. These include diisopropylamino, methylaminohexyl, and aminodecyl.

The aryl groups include the phenyl and naphthyl groups and substituted derivatives. Substituted alkyl derivatives include toluyl, xylyl, pseudocumyl, mesityl, isodurenyl, durenyl, pentamethylphenyl, ethylphenyl, n-propylphenyl, cumyl, styryl, allylphenyl, Nitro- and halo-substituted may be exemplified by chloronitrophenyl, chlorodinitrophenyl, dinitrotoluol, and trinitroxylyl.

Amine-substituted components include methylaminotoluyl, trimethylaminophenyl, diethylaminophenyl, aminomethylphenyl, diaminophenyl, ethoxyaminophenyl, chloroaminophenyl, bromoaminophenyl and phenylaminophenyl. Halo-substituted aryl groups include fluoro-, chloro-, bromo-, iodophenyl, chlorotoluyl, bromotoluyl, methoxybromophenyl, dimethylaminobromophenyl, trichlorophenyl, bromochlorophenyl, and bromoiodophenyl.

Groups derived from aromatic carboxylic acids are also useful. These include methylcarboxylphenyl, dimethylaminocaboxyltoluyl, laurylcarboxyltoluyl, nitrocarboxyltoluyl, and aminocarboxylphenyl. Groups derived from substituted alkyl esters and amides of benzoic acid may also be used. These include aminocarboxylphenyl and methoxycarboxyphenyl.

Titanates wherein R' is an epoxy group include tall oil epoxides (a mixture of 6 to 22 carbon alkyl groups)

containing an average of one epoxy group per molecule and glycidol ethers of lauryl or stearyl alcohol.

Substituted naphthyl groups include nitronaphthyl, chloronaphthyl, aminonaphthyl and carboxynaphthyl groups.

R' has a total of up to 14 carbon atoms. For example, each R' may be isopropenyl, vinyl, 2-aminoethyl, 1-aminopropyl, hydroxymethyl, 2,2-dichloroethyl, trimethoxymethyl, cyanomethyl and acetylmethyl.

Examples of the organotitanates of the invention are: $(i-C_3H_7O)Ti[OCOC(CH_3)=CH_2]_3$; $(i-C_3H_7O)Ti(OCOCH_2NH_2)_3$; $(C_6H_{11}O)Ti(OCOCH_2OCH_3)_2(OCOCHClCH_3)$; $(CH_3O)Ti(OCOCCl_3)_3$; $(C_2H_5O)Ti(OCOCHBrCH_2Cl)(OCOC_6H_5)(OCOCH_3NH_2)$; and $(i-C_3H_7O)Ti(OCOC_2H_5)(OCOCH_2CN)[OCOCH_2N(CH_3)_2]$.

Another composition of matter of the invention comprises the reaction products of the aforesaid classes of alkoxy titanium salts with inorganic materials, especially when $x$ in the above formula is 3. The amount of the titanate reacted is at least 0.01 part, preferably from 0.1 to 5 parts, and most preferably between 0.2 and 2 parts, per 100 parts of inorganic solid. The optimum proportions required are a function of the inorganic solid and the alkoxy titanium salt selected, and the degree of the comminution, i.e., the effective surface area, of the inorganic solid. The reaction of the titanate takes place on the surface of the inorganic filler. The RO group splits off and an organic hydrophobic surface layer is formed on the inorganic solid. The unmodified inorganic solid is difficult to disperse in an organic medium because of its hydrophilic surface. The organotitanium compound may be incorporated into an organic medium (low molecular weight liquids or higher molecular weight polymeric solids) with the inorganic solid. Alternatively, the organo-titanates may be first reacted with the inorganic solid in the absence of an organic medium and thereafter admixed with the latter.

By means of the present invention, the dispersion of inorganic materials in organic polymer media is improved and achieves (1) improved rheology or higher loading of the dispersate in the organic medium; (2) higher degrees of reinforcement by the use of fillers, thereby resulting in improved physical properties in the filled polymer; (3) more complete utilization of chemical reactivity, thereby reducing the quantity of inorganic reactive solids required; (4) more efficient use of pigments and opacifiers; (5) higher inorganic-to-organic ratios in a dispersion; and (6) shorter mixing times to achieve dispersion.

Also, according to the invention herein, the reaction with the single RO group may be carried out neat or in an organic medium to form a liquid, solid, or pastelike solid dispersion which can be used in the compounding of the final polymeric system. Such dispersions are very stable, i.e., having little tendency to settle, separate, or harden on storage to a non-dispersible state.

Moreover, the invention simplifies the making of inorganic dispersions in organic media by providing a means to eliminate the solvent, to reduce the cost of processing equipment, and to reduce the time and energy required to disperse an inorganic solid material in a liquid or polymeric organic solid.

The present invention results in the formation of a reinforced polymer which has a lower melt viscosity, improved physical properties, and better pigmenting characteristics than the prior art materials.

The practice of the present invention achieves a product comprising natural or synthetic polymers which contain particulate or fibrous inorganic materials which reinforce, pigment or chemically react with the polymer to produce a product having superior physical properties, better processing characteristics, and more efficient utilization of pigments.

Amongst the advantages gained by the practice of this embodiment of the present invention is the option of dispensing with the use of volatile and flammable solvents and the attendant need to dry the filler or to recover solvents. Furthermore, multi-molecular layer formation is minimized. Also, the dispersions of the present invention are non-oxidizing.

The inorganic materials may be particulate or fibrous and of varied shape or size, so long as the surfaces are reactive with the hydrolyzable group of the organotitanium compound. Examples of inorganic reinforcing materials include metals, clay, carbon black, calcium carbonate, barium sulfate, silica, mica, glass and asbestos. Reactive inorganic materials include the metal oxides of zinc, magnesium, lead, and calcium and aluminum, iron filings and turnings, and sulfur. Examples of inorganic pigments include titanium dioxide, iron oxides, zinc chromate, ultramarine blue. As a practical matter, the particle size of the inorganic materials should not be greater than 1 mm, preferably from 0.1 micron to 500 micron.

It is imperative that the alkoxy titanium salt be properly admixed with the inorganic material to permit the surface of the latter to react sufficiently. The optimum amount of the alkoxy titanium salt to be used is dependent on the effect to be achieved, the available surface area of and the bonded water in the inorganic material.

Reaction is facilitated by admixing under the proper conditions. Optimum results depend on the properties of the alkoxy titanium salt, namely, whether it is a liquid or solid, and its decomposition and flash points. The particle size, the geometry of the particles, the specific gravity, the chemical composition, among other things, must be considered. Additionally, the treated inorganic material must be thoroughly admixed with the polymeric medium. The appropriate mixing conditions depend on the type of polymer, whether it is thermoplastic or thermosetting, its chemical structure, etc., as will be readily understood by those skilled in the art.

Where the inorganic material is pretreated with the organic titanate, it may be admixed in any convenient type of intensive mixer, such as a Henschel or Hobart mixer or a Waring blender. Even hand mixing may be employed. The optimum time and temperature are determined to obtain substantial reaction between the inorganic material and the organic titanate. Mixing is performed under conditions at which the organic titanate is in the liquid phase, at temperatures below the decomposition temperature. While it is desirable that the bulk of the hydrolyzable groups be reacted in this step, this is not essential where the materials are later admixed with a polymer, since the substantial completion of the reaction may take place in this latter mixing step.

Polymer processing, e.g., high shear mixing, is generally performed at a temperature well above the second order transition temperature of the polymer, desirably at a temperature where the polymer will have a low melt viscosity. For example, low density polyethylene is best processed at a temperature range of 170° to 230° C.; high density polyethylene from 200° to 245° C.;

polystyrene from 230° to 260° C.; and polypropylene from 230° to 290° C. Temperatures for mixing other polymers are known to those skilled in the art and may be determined by reference to existing literature. A variety of mixing equipment may be used, e.g., two-roll mills, Banbury mixers, double concentric screws, counter or co-rotating twin screws and ZSK type of Werner and Pfaulder and Busse mixers.

When the organic titanate and the inorganic materials are dry-blended, thorough mixing and/or reaction is not readily achieved and the reaction may be substantially completed when the treated filler is admixed with the polymer. In this latter step, the organic titanate may also react with the polymeric material if one or more of the R' groups is reactive with the polymer.

To illustrate further the invention, attention is directed to the following examples. In certain of these examples, the number of ligands per molecule is expressed for a mixed number. In such cases, it should be understood that the structural formula represents a blend of compounds and the mixed number is the average number of such ligands in the blend.

To illustrate further the invention, the following example shows the preparation of a compound within the scope of formula above:

EXAMPLE A: PREPARATION OF ORGANO-TITANATE ESTERS

One mole of tetraisopropyl titanate is added to a pyrex-lined metal vessel, equipped with an agitator, internal heating and cooling means, a vapor condenser and a distillate trap, and stirring commenced. Liquid methacrylic acid is added at a controlled rate so that the exothermic reaction is maintained below about 180° C. until 3.50 moles of the acid are added. Isopropanol is removed from the reaction product by distillation at 150° C. at 50 mm Hg to remove volatiles.

The organic titanate thus produced has an average of 3.3 moles of methacrylate per molecule. The product structure is determined by ascertaining the isopropanol liberated from the reaction and the residual methacrylic acid. From 3.1 to 3.3 moles of isopropanol are recovered. About 0.2 mole methacrylic acid plus isopropyl methacrylate are detected. The physical properties of the product are:

| | |
|---|---|
| Specific Gravity at 24° C. | 0.92 |
| Flash Point (COC), ° C. | 120 |
| Pour Point, ° C. | About 130 |
| Decomposition Point, ° C. | Above 200 |
| Appearance | Tan Solid |

The following examples illustrate the use of the alkoxy titanium salts of the instant invention as coupling agents in inorganic-filled polymer systems. All parts are by weight unless otherwise indicated.

EXAMPLE 1

This example shows a comparison of property modification using compounds of the instant invention and commercially available trialkoxy vinyl silane coupling agent $CH_2=CH\ Si(OCH_2CH_2OCH_3)_3$ in clay-filled peroxide-cured ethylene-propylene-diene terpolymer (EPDM). The compound of the invention used was the formula $(i-C_3H_7O)_{0.7}Ti[OCOC-(CH_3)=CH_2]_{3.3}$. Four formulations were prepared. Each contained 100 parts by weight of EPDM (Vistalon 2504, a trademark of Exxon Corporation), 1.5 parts of an antioxidant (Agerite Resin D, a trademark of R. T. Vanderbilt Co., Inc.), 5 parts of zinc oxide, 20 parts of an aliphatic extender oil (Sunpar 2280, a trademark of Sun Oil Company), 5 parts of a 5:1 by weight paste of red lead in a viscous oil, and 6 parts of dicumyl peroxide. In addition to the above, Composition 1 contained 90 parts of a hard clay pretreated with 1% of the aforementioned silane plus 2 parts per weight of the silane; Composition 2 contained 90 parts by weight of a silane-pretreated commercially available hard clay and 2 parts by weight of the compound of the invention; and Composition 3 contained hard clay pretreated with 1% by weight of the aforementioned titanate plus 2 parts by weight of the titanate. Composition 4 was identical to Composition 3, except that only 10 parts of the aliphatic extender oil were employed.

The aforesaid compositions were cured for 20 minutes at 171° C. The following Table shows the results obtained.

TABLE A

| Original Properties | Composition No. | | | |
|---|---|---|---|---|
| | 1 | 2 | 3 | 4 |
| 200% Modulus, psi | 495 | 377 | 438 | 684 |
| 300% Modulus, psi | 803 | 576 | 605 | 862 |
| Tensile, psi | 940 | 1000 | 1009 | 1048 |
| Elongation at Break, % | 381 | 740 | 750 | 527 |
| Shore A Hardness | 60 | 62 | 63 | 67 |

The aforesaid Table clearly shows the advantages of the invention as compared to the use of silane coupling agents. Compositions Nos. 2, 3 and 4 showed increased elongation at the break and Compositions 2 and 3 increased hardness. Also, Composition 4 showed increased modulus and tensile strength as compared to the silane composition. It is particularly noteworthy that Composition 4 shows 38% greater elongation at the break, despite the elimination of 50% of the aliphatic extender oil plasticizer.

EXAMPLE 2

This example teaches the use of compounds of this invention, viz., (R) $(CH_3O)Ti(OCOCH=CH_2)_3$ and (S) $(i-C_3H_7O)Ti[OCOC-(CH_3)=CH_2]_3$ as flex property modifiers for polyester resin.

Formulations were prepared containing 100 parts of a cobalt activated polyester resin (GR 643, a trademark of W. R. Grace Co.), 1 part of methyl ethyl ketone peroxide, 60 parts of high surface area calcium carbonate, and 0.3 part of alkoxy titanium salt, as indicated in the Table below.

Samples measuring ½ inch × 5 inches × ⅛ inch thick were cast and cured at ambient temperature for 30 minutes. The castings were tested and the results shown in Table B below:

TABLE B

| Alkoxy Titanium Salt | Flex Modulus psi | Flexural Strength psi |
|---|---|---|
| None | $1.5 \times 10^6$ | $4 \times 10^3$ |
| R | $3.5 \times 10^6$ | $7 \times 10^3$ |
| S | $4.0 \times 10^6$ | $10 \times 10^3$ |

The above data establish clearly the improved flexural properties obtained by the use of the organotitanates of the invention.

Having thus described out invention, what we claim and desire to protect by Letters Patent is:

1. A filled polymeric composition which comprises a peroxide-cured polymer containing therein a filler treated with a compound having the formula (RO)-Ti(OCOR')₃ wherein R is a monovalent alkyl, alkenyl, alkynyl, or aralkyl group having from 1 to 30 carbon atoms or a substituted derivative thereof and R' is a monovalent organic group, the total number of carbon atoms in the three R' groups in a molecule being not more than 14.

2. The filled polymeric composition of claim 1 wherein R' is vinyl, methylvinyl or aminomethyl group and R is an alkyl group having 1 to 6 carbon atoms.

3. The filled polymeric composition of claim 1 wherein the filler is an inorganic material which is a metal, metal oxide, carbon black, sulfur, calcium carbonate, silica or clay.

4. The filled polymeric composition of claim 3 wherein the metal oxide is zinc oxide, magnesium oxide, titanium oxide, yellow iron oxide, calcium oxide, or lead oxide.

5. The filled polymeric composition of claim 1 wherein the polymeric material is an EPDM rubber or a polyester resin.

6. A filled peroxide-cured polyester composition which comprises a polyester resin containing an organo-titanate compound having the formula (RO)-Ti(OCOR')₃ wherein R is an alkyl group having 1 to 6 carbon atoms and R' is a vinyl or a methylvinyl group.

7. The filled polyester composition of claim 6 wherein the R group is isopropyl.

8. The filled polyester composition of claim 6 wherein there is present 0.1 to 5 parts of the organo-titanate compound per 100 parts of filler.

* * * * *